United States Patent
Graban et al.

(10) Patent No.: US 10,031,143 B2
(45) Date of Patent: Jul. 24, 2018

(54) METHOD FOR THE COMPARISON OF PROTEIN HIGHER ORDER STRUCTURES

(71) Applicants: RECLAIMRX, LLC, Bloomington, IN (US); UNIVERSITY OF MASSACHUSETTS, Boston, MA (US); Eric M. Graban, Bloomington, IN (US); Richard Vachet, Belchertown, MA (US)

(72) Inventors: Eric M. Graban, Bloomington, IN (US); Richard Vachet, Belchertown, MA (US); Yuping Zhou, Carmel, IN (US)

(*) Notice: Subject to any disclaimer, the term of this patent is extended or adjusted under 35 U.S.C. 154(b) by 0 days.

(21) Appl. No.: 15/312,434

(22) PCT Filed: May 21, 2015

(86) PCT No.: PCT/US2015/032081
§ 371 (c)(1),
(2) Date: Nov. 18, 2016

(87) PCT Pub. No.: WO2015/179714
PCT Pub. Date: Nov. 26, 2015

(65) Prior Publication Data
US 2017/0122963 A1  May 4, 2017

Related U.S. Application Data

(60) Provisional application No. 62/001,303, filed on May 21, 2014.

(51) Int. Cl.
| | |
|---|---|
| A61K 38/00 | (2006.01) |
| C07K 2/00 | (2006.01) |
| C07K 4/00 | (2006.01) |
| C07K 5/00 | (2006.01) |
| C07K 7/00 | (2006.01) |
| C07K 14/00 | (2006.01) |
| C07K 16/00 | (2006.01) |
| C07K 17/00 | (2006.01) |
| G01N 33/68 | (2006.01) |

(52) U.S. Cl.
CPC ..... *G01N 33/6848* (2013.01); *G01N 2560/00* (2013.01)

(58) Field of Classification Search
CPC ... G01N 33/6848; G01N 2560/00; C07K 1/13
See application file for complete search history.

(56) References Cited

U.S. PATENT DOCUMENTS

2003/0077616 A1  4/2003  Lomas

FOREIGN PATENT DOCUMENTS

WO  WO2004/086050  10/2004

OTHER PUBLICATIONS

Mendoza, VL et al., Probign Proetin Structure by Amino Acid-Specific Covalent Labeling and Mass Spectrometry, Mass Spectrom Rev. 2009, vol. 28, 61 pages.
Zhou, Y., Structural Analysis of Proteins by Covalent Labeling and Mass Spectrometric Detection, University of Masssachusetts Amherst, Doctoral Dissertation, Feb. 2014, 100 pages.
Zhou, Y. et al., Covalent Labeling with Isotopically Encoded Reagents for Faster Structural Analysis of Proteins by Mass Spectrometry, Analytical Chemistrly, Oct. 15, 2013, vol. 85, No. 20, 16 pages.
International Search Report and Written Opinion dated Sep. 15, 2015 in PCT/US2015/032081, 10 pages.
European Search Report for European Application No. 15795963.6 dated Nov. 3, 2017, 9 pages.
Yuping Zhou et al., "Diethylpyrocarbonate Labeling for the Structural Analysis of Proteins: Label Scrambling in Solution and How to Avoid It," Journal of the American Society for Mass Spectrometry, vol. 23, No. 5, dated Feb. 14, 2012, 9 pages.
Yuping Zhou et al., "Increased Protein Structural Resolution from Diethylpyrocarbonate-based Covalent Labeling and Mass Spectrometric Detection," Journal of the American Society for Mass Spectrometry, vol. 23, No. 4, dated Feb. 2, 2012, 10 pages.
Vanessa Lee Mendoza et al., "Protein Surface Mapping Using Diethylpyrocarbonate with Mass Spectrometry Detection," Analytical Chemistry, vol. 80, No. 8, dated Apr. 1, 2008, 10 pages.
Carey A. Hobbs et al., "Structural Characterization of the Conformational Change in Calbindin-D 28k upon Calcium Binding Using Differential Surface Modification Analyzed by mass Sepcrometry," Biochemistry, vol. 48, No. 36, dated Sep. 15, 2009, 28 pages.

*Primary Examiner* — Marcela M Cordero Garcia
(74) *Attorney, Agent, or Firm* — Faegre Baker Daniels LLP

(57) ABSTRACT

Some aspects of the disclosure include methods for comparing the higher order structures (HOS) of proteins using covalent labeling agents which allow for the direct comparison of changes in the HOS of protein therapeutics using mass spectrometry. The inventive methods can be used to access the effect of changing the process of producing and/or storing complex biologic compounds as well as determining if the HOS of a protein therapeutic has spontaneously changed during storage. Still other uses include comparing branded biologic therapeutic compounds to biosimilar compounds, and measuring changes in the aggregation states of proteins.

19 Claims, 9 Drawing Sheets

Modification percentage of amino acids at oxidative condition vs native condition.

Modification percentage of amino acids at thermal degradation condition vs native condition.

Modification percentage of amino acids at thermal condition vs native condition.

Modification percentage of amino acids at thermal condition vs native condition.

Modification percentage of amino acids at thermal condition vs native condition.

Modification percentage of specific amino acids under different degradation conditions.

Size exclusion chromatography of β-2-Microglobulin after 1 day at 75°C

Size exclusion chromatography of β-2-Microglobulin after exposure to 10% hydrogen peroxide

METHOD FOR THE COMPARISON OF PROTEIN HIGHER ORDER STRUCTURES

PRIORITY CLAIM

This application is a U.S. National Phase filing of PCT/US2015/032081, filed May 21, 2015, which claims the benefit of U.S. Provisional Application No. 62/001,303, filed May 21, 2014, the entire disclosures of both of which are hereby expressly incorporated by reference herein.

FIELD OF THE INVENTION

The present invention relates to the characterization of the higher order structure of proteins, and their comparison to determine the presence and extent of differences in their higher order structures.

BACKGROUND AND SUMMARY

Proteins represent an important and growing class of therapeutic compounds. Many vitally important therapeutic compounds for treating human and animal diseases and other conditions are currently in the market place and many more are in development. One challenge presented by proteins in general and proteins used as therapeutics in particular is obtaining an accurate understanding of their higher order structure (HOS), and ensuring that this HOS remains unchanged throughout the development and commercialization lifecycle of the drug. Examples include determining the impact of changes to manufacturing, shipping, or storage conditions on the higher order structure of proteins. Still other examples include determining the structural similarities between proposed biosimilar therapeutic compounds and the putatively bio-equivalent approved protein therapeutic.

However, the inherent complexity of protein structures presents challenges that must be addressed in order to accomplish high resolution analysis of higher order structures of proteins. Various methods have been developed in an attempt to overcome these challenges. These challenges increase exponentially when subtle changes in the protein's structure can affect its biological properties and when cost is factored into the process.

Aspects of the invention disclosed herein, seek to address these challenges.

A first set of embodiments includes methods for detecting changes in the higher order structure of proteins, comprising the steps of treating a reference protein with a first compound, under a defined set of conditions, wherein the treating step produces a covalently labeled reference protein; contacting a target protein with the first compound, under the defined set of conditions, wherein the contacting step produces a covalently labeled target protein, wherein the reference protein and the target protein have identical primary structures; and analyzing the covalently labeled target protein and the covalently labeled reference protein by mass spectrometry.

A second set of embodiments includes the methods according to the first set of embodiments, further including the steps of comparing the results of the analysis of the covalently labeled reference protein and the covalently labeled target protein; and concluding that there is a difference in the higher order structure of the reference protein and the target protein if a difference is detected in the comparing step.

A third set of embodiments includes the methods according to the first through the second set of embodiments, wherein the reference protein and the target protein includes at least one amino acid selected from the groups consisting of cysteine, histidine, lysine, tyrosine, serine, threonine, aspartic acid, and glutamic acid.

A fourth set of embodiments includes the methods according to the first through the third set of embodiments, wherein the target protein is selected from the group of proteins consisting of antibodies, enzymes, ligands, or regulatory factors.

A fifth set of embodiments includes the methods according to the first through the fourth set of embodiments wherein the reference protein has not been exposed to the same processing or the same manufacturing steps as the target protein.

A sixth set of embodiments includes the methods according to the first through the fourth set of embodiments, wherein the target protein has been stored in a suspension buffer designed to stabilize the reference protein, or in a lyophilized form for a period of time longer than the time that the reference protein has been stored in the suspension buffer or in a lyophilized form.

A seventh set of embodiments includes the methods according to the sixth set of embodiments, wherein the suspension buffer include at least one claims of reagent selected from the group of reagents comprising: phosphate, amino acids, inorganic salts, surfactants, metal chelators, polymers, inert proteins, and preservatives.

An eighth set of embodiments includes the methods according to the sixth through the seventh set of embodiments, wherein the suspension buffer has a pH in at least one pH range selected from the group consisting of, between about 2.0 to about 10.0; between about 2 to about 9.0; between 3 to about 10.0; between 3 to about 8.0; between about 3.5 to about 7.5; between about 4.5 to about 6.5; and between about 5.5 to about 7.3.

A ninth set of embodiments includes the methods according to the sixth through the eighth sets of embodiments, wherein the suspension buffer includes at least one of the following amino acids selected from the group consisting of histidine, arginine, glycine, methionine, proline, lysine, glutamic acid, alanine, and arginine mixtures.

A tenth set of embodiments includes the methods according to the sixth through the ninth sets of embodiments, wherein the suspension buffer includes at least one of the following inorganic salts selected from the group consisting of sodium chloride, calcium chloride, and magnesium chloride.

An eleventh set of embodiments includes the methods according to the sixth through the tenth sets of embodiments, wherein the suspension buffer includes at least one of the surfactants selected from the group consisting of polysorbates, SDS, Brij 35, and Triton X-10.

A twelfth set of embodiments includes the methods according to the sixth through the eleventh sets of embodiments, wherein the suspension buffer includes EDTA as a metal chelator.

A thirteenth set of embodiments includes the methods according to the sixth through the twelfth sets of embodiments, wherein the suspension buffer includes at least one of the following polymers selected from the group consisting of polyethylene glycols (PEGs) and polysaccharides.

A fourteenth set of embodiments includes the methods according to the sixth through the thirteenth sets of embodiments, wherein the suspension buffer includes at least one of the following inert proteins selected from the group consisting of dextran, hydroxyl ethyl starch (HETA), PEG-4000, and gelatin.

A fifteenth set of embodiments includes the methods according to the sixth through the fourteenth sets of embodiments, wherein the suspension buffer includes at least one of the following preservatives selected from the group consisting of benzyl alcohol, m-cresol, and phenol.

A sixteenth set of embodiments includes the methods according to the first through the fifteenth sets of embodiments, wherein the compound used to label the reference protein and the target protein is diethylpyrocarbonate.

A seventeenth set of embodiments includes the methods according to the first through the sixteenth sets of embodiments, wherein the proteins being labeled are proteins with a molecular weight of at least 5 kDa.

An eighteenth set of embodiments includes the methods according to the first through the sixteenth sets of embodiments, wherein the proteins being labeled are proteins with a molecular weight of at least 12 kDa.

A nineteenth set of embodiments includes the methods according to the first through the eighteenth set of embodiments, wherein the proteins being labeled are therapeutic proteins.

A twentieth set of embodiments includes the methods according to the first through the eighteenth set of embodiments, wherein the proteins being labeled are monoclonal antibodies.

A twenty-first set of embodiments includes the methods according to the first through the twentieth set of embodiments, further including the step of determining the fraction of the amino acids in the target protein that are labeled as a function of the concentration of the protein and/or the concentration of the compound in the contacting step. In some of these embodiments the compound is DEPC.

A twenty-second set of embodiments includes the methods according to the first through the twenty-first set of embodiments, wherein in the fraction of the amino acids in the target protein modified by the compound is determined as a function of the time that the target protein and the compound are in contact with one another. In some of these embodiments the compound is DEPC.

A twenty-third set of embodiments includes the methods according to the first through the twenty-second set of embodiments, wherein one or more of the proteins in the assay has undergone partial degradation or denaturing.

A twenty-fourth set of embodiments includes the methods according to the first through the twenty-third set of embodiments, wherein the onset and growth of protein aggregates is monitored by % labeling at one or more amino acids where % labeling correlates with aggregation.

A twenty-fifth set of embodiments includes a means for comparing the HOS of proteins, comprising the steps of labeling a reference protein with a covalent label, to form a labeled reference protein; tagging a target protein with the covalent label, to form a labeled target protein, wherein both the reference protein and the target protein are treated with at least one reagent that covalently labels the proteins; analyzing both the labeled reference protein and the labeled target protein by use of the same mass spectrometry; and comparing the mass spectra of the labeled reference protein and labeled target protein to one another, wherein said reference protein and said target protein are substantially similar to one another.

A twenty-sixth set of embodiment includes the means according to the twenty-fifth set of embodiments, wherein the reagent that covalently labels the reference protein and the target protein is diethypyrocarbonate.

In some embodiment of the invention a sample of a protein in its unaltered state is digested and analyzed to determine the peptide map. Digestion consists of combining and incubating the protein with a preotolytic enzyme, such as trypsin or chymotrypsin. The enzyme is quenched, and, after workup, the peptides analyzed via mass spectrometry.

In some embodiments a sample of the protein in its unaltered state (ie—the reference protein) is then covalently modified. Modification may include first identifying covalent labels most suitable for labeling the protein of interest based on the amino acid makeup of the protein. If more than one covalent label is to be used, each may be combined with the protein separately, or combined with the protein at the same time. A sample of the protein is combined with the covalent label in an appropriate buffer solution. In some embodiments of these methods, samples are collected from the solution as a function of time so that the % incorporation of the label can be tracked. In other embodiments of this method, multiple sample preparations will occur, with the relative concentrations of the protein and covalent label varying in each preparation, and samples collected from each of the preparations after the same elapsed reaction time. In this case, the % incorporation of the label can be tracked as a function of covalent label concentration. This approach is often used when the covalent label can degrade in the reaction solution, such as when an anhydride label is used in an aqueous buffer solution. Each sample is digested and analyzed via mass spectrometry as described above. Comparison of the mass spectrometry results from the covalent labeling experiments vs. the initial peptide mapping experiments will allow for identification of the residues that are modified by the covalent label, and the extent of modification at each residue as a function of time and/or concentration. The results from multiple labels can be combined to give a more complete description of the overall protein HOS.

In some embodiments a sample of the target protein is then subjected to the same covalent labeling method as described for the reference protein. The mass spectrometry results for the target protein can then be compared to the reference protein, with the location of labeling, and the extent of labeling as a function of time and/or concentration, compared. Changes in the location and/or % incorporation indicate a change in the HOS structure of the target protein vs. the reference protein.

Some embodiments of the invention include methods for determining the higher order structure of proteins, comprising the steps of: contacting at least a portion of a target protein with a covalent label in order to produce a covalently labeled target protein; modifying a reference protein with the same covalent label in order to produce a labeled reference protein; analyzing the covalently labeled target protein and the labeled reference protein by use of the same mass spectrometry technique; and comparing the results of the analysis of the covalently labeled target protein to a reference protein, in order to determine if there is a detectable difference between the labeled target protein and the labeled reference protein.

In some embodiments of the invention the target proteins includes at least one amino acid selected from the groups consisting of cysteine, histidine, lysine, tyrosine, serine, threonine, aspartic acid, and glutamic acid. In some embodiments a single covalent label is used to create the covalently labeled target protein. In other embodiments two or more different covalent labels are used to create the covalently labeled target protein, and wherein the results of the individual covalent bond analyses are combined to increase the fraction of amino acids in the target proteins that are measured in a given assay.

In some embodiments the methods further include the step of determining the fraction of the amino acids in the target protein that are labeled as a function of the concentration of the protein and/or the concentration of covalent label modifier in the contacting step. In some embodiments the fraction of the amino acids in the target protein modified by the covalent labels is determined as a function of the time that the target protein and at least one covalent label are in contact with one another. In some embodiments the inventive methods are carried out using proteins, especially target proteins, that may have undergone partial degradation or denaturing.

Still other embodiments of the invention include means for comparing the HOS of proteins, comprising the steps of: labeling a reference protein with a covalent label, to form a labeled reference protein; tagging a target protein with the covalent label, to form a labeled target protein; analyzing both the labeled reference protein and the labeled target protein by use of the same mass spectrometry; and comparing the mass spectra of the labeled reference protein and labeled target protein to one another, wherein said reference protein and said target protein are substantially similar to one another.

DESCRIPTION

Figure 1:
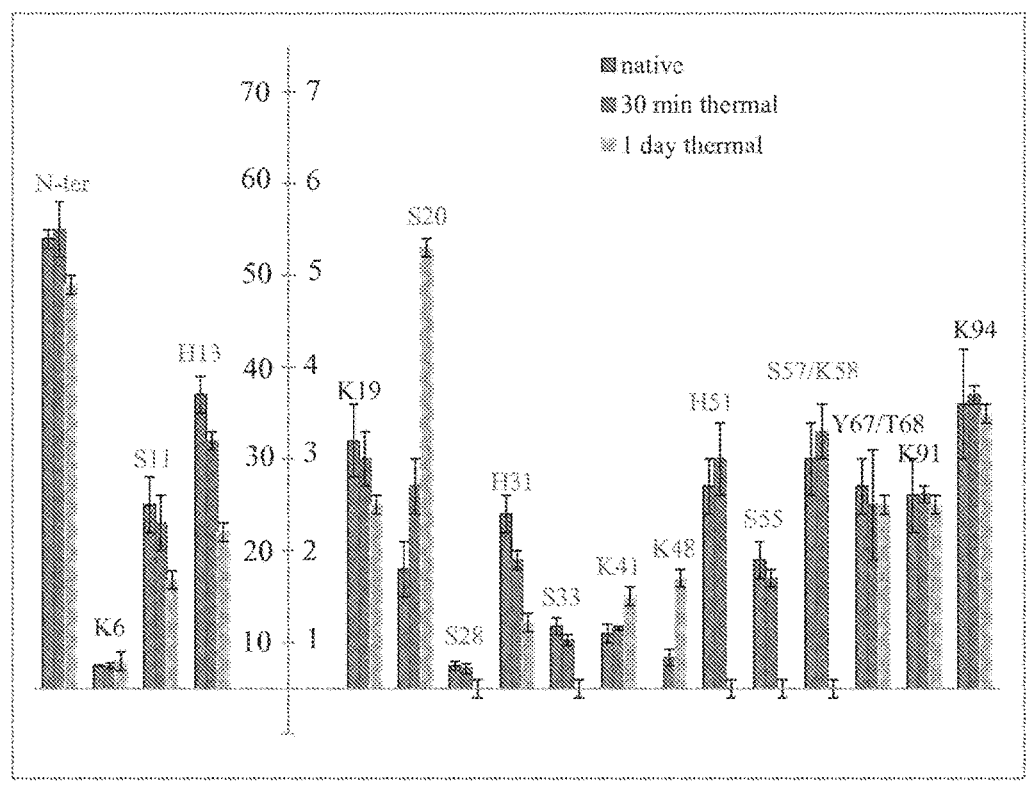
FIG. 1. Bar graph illustrating results from diethylpyrocarbonate (DEPC) labeling of β-2-microglobulin that has undergone thermal degradation.

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates are within the scope of this disclosure and the claims.

Unless explicitly defined otherwise or clearly intended otherwise, all terms used herein given the customary meaning in the art.

As used herein, unless explicitly stated otherwise or clearly implied otherwise the term 'about' refers to a range of values plus or minus 10 percent, e.g. about 1.0 encompasses values from 0.9 to 1.1.

As used herein, unless clearly stated otherwise, higher order structure (HOS) refers to secondary and tertiary protein structure, i.e., how amino acid residues and primary structures are arranged in three-dimensional space relative to one another. It is understood that changes in secondary and tertiary structure of a protein may impact quaternary structure of protein complexes that include the relevant protein.

The highest resolution methods for determining the 3-dimensional structure of proteins include X-ray crystallography and NMR. However, many proteins are not amenable to these methods. X-ray crystallography is limited by the need to crystallize proteins for analysis (not all proteins can be coaxed into crystallizing), and by the static nature of this method in which only the crystalline form of the protein is analyzed. This has been shown to be problematic as the most stable crystalline form is not necessarily indicative of the dynamic nature of the protein structure in solution. (Johnson and Suizdak *Nature Structural Biology*, 1999, 6(2), 114-116).

While NMR analyses of protein structures are performed on proteins in solution, NMR also suffers from limited effectiveness with high molecular weight proteins and the need to incorporate isotopic labelling, which is expensive and time-consuming, to obtain HOS information.

In addition, both X-ray crystallography and NMR may require large amounts of protein, which can be problematic when only limited sample amounts are available or when the compounds are expensive to manufacture. As a result, these methods have only been applied to a limited number of proteins whose sequences are currently known. (Reilly, *Anal Biochem*, 2007, 367, 13-19)

Spectroscopic methods, such as FTIR, UV, fluorescence, or CD, are also commonly used to analyze protein higher order structures. These approaches suffer from a lack of precision as the methods are not able to resolve protein structures to the level of individual peptides or amino acids, but are instead limited to larger structural characteristics, such as the extent of alpha helix or beta sheet. (For an example of this, see Ehrard *Biochemistry*, 1996, 35, 9097-9105)

Mass Spectrometry Analysis of Proteins.

Mass spectrometry has emerged as a powerful method for protein HOS analysis as it is able to provide amino acid level resolution for proteins analysis; it can also accommodate large proteins, proteins with high conformational flexibility, does not require incorporation of isotopic labeling, and may be performed using small sample sizes.

Many mass spectrometry techniques for determining the structure of proteins involve changing the mass of the protein or its proteolytic fragments in a manner that is dependent upon the 3-dimensional structure of the protein. In some instances this may be accomplished by contacting the protein with an agent that modifies the protein. In many instances the extent of modification is a function of the solvent accessibility of different regions of the protein. Using these methods, greater rates of modification occur in regions of the protein that have higher solvent access and thus greater contact with the modifying agent. Factors that impact contact include solvent accessibility, protein folding patterns, and protein interaction with target/receptor agents.

A typical mass spectrometry analysis may begin with peptide mapping of a sample of isolated protein in its natural state to serve as a reference. When carried out in solution, the peptide map can show the extent of solvent accessibility for the peptides or residues of interest via measurement of the extent of modification at these sites. The protein can then be studied in the system of interest (for example, introducing the protein to potential binding agents to determine the extent and location of binding). Subsequent comparison of the protein's peptide map vs. that of the isolated protein peptide map allows for direct comparison of solvent accessibility at each peptide or residue. Changes in the extent of modification can then be attributed to changes in the protein HOS, or to the binding of the impacted regions to receptors that can impede access to solvent based modifying agents. This approach has been useful in conducting protein surface structural analysis, protein-ligand complex analysis, and protein-protein complex analysis.

Methods commonly employed for the mass spectrometric analysis of proteins include hydrogen/deuterium (H/D) exchange, hydroxyl radical footprinting, cross-linking, and amino acid specific covalent labeling.

The H/D exchange strategy entails the use of $D_2O$ as a labeling agent, exploiting the rapid exchangeability of the labile amide hydrogen atoms or non-aliphatic side chain hydrogen atoms in contact with hydrogen bonded aqueous protons or deuterons. In this approach, the labile hydrogen atoms exchange with deuterium atoms, resulting in incorporation of deuterium into the protein backbone or side chain. Subsequent proteolytic cleavage and mass spectrometric analysis can detect the extent of deuterium incorporation into the protein, allowing for solvent accessibility determinations to be made as described above. See for example, U.S. Pat. No. 5,658,739, which is incorporated herein by reference in its entirety.

The benefits of H/D exchange include the potential ability to measure protein dynamics with high resolution as each amino acid has an amide functional group as part of the protein backbone, and the small size of $D_2O$ which allows for greater access to portions of the protein that might have limited access to larger molecules (for examples, amino acids inside of protein folds). However, this approach suffers from the ability of the deuterium that has been incorporated into the protein to back-exchange with solvent based hydrogen atoms. Back exchange can occur at numerous points during the analysis, including sample preparation for HPLC/MS analysis and sample exposure to $H_2O$ based mobile phase. Various strategies are employed to mitigate back exchange, including conducting the H/D exchange, proteolysis, and mass spectrometric analysis at cold temperatures and with strict control of the pH of the exchanged sample. The effectiveness of these strategies can be technique dependent, or require the use of specialized, automated mass spectrometry systems. An additional challenge imposed by the strict temperature and pH requirement is the need to perform proteolysis with proteolytic enzymes such as pepsin, which may lack a high level of substrate specificity which results in enzymatic digestions that create large number of peptides thereby generating complex data sets requiring painstaking analysis. (Reilly Anal. Chem. 2005, 77, 7274-7281)

The Hydroxyl Radical Footprinting (HRF) strategy uses hydroxyl radicals as the labeling agent. In this method, hydroxyl radicals are generated from hydrogen peroxide in the presence of the protein via laser excitation or are produced via X-ray irradiation of water. HRF provides high resolution measurements as hydroxyl radicals can form covalent bonds with the side chains of any amino acid, although the rates of addition vary significantly. Subsequent proteolytic cleavage and mass spectrometric analysis can detect the extent of hydroxyl radical incorporation into the protein, allowing for solvent accessibility determinations to be made as described above.

The benefits of HRF include the potential ability to label almost any amino acid in a protein, and the irreversibility of the covalent bond formed, which removes the need to mitigate for back exchange as in H/D Exchange. However, HRF requires specialized equipment (i.e. a laser or synchrotron source) to generate hydroxyl radicals. In addition, data analysis is challenging as hydroxyl radical labeling can produce over 50 different types of products, which also reduces the sensitivity of the method.

The Cross-Linking strategy uses bifunctional or trifunctional molecules to attach to two separate amino acid side chains within a protein structure. Two of the functional groups on the cross-linking agents form bonds with two different amino acid side chains that are nearby in three-dimensional space. Different cross-linking agents vary in terms of the distance between the reactive functional groups, so that information regarding the distance between residues on the protein can be ascertained by their ability to attach to each end of the cross-linking label. While this method provides spatial information regarding protein structure, surface coverage is often limited, and data analysis is extremely challenging.

The amino acid specific covalent labeling strategy utilizes small molecules that can form covalent bonds with the functional groups of specific amino acid side chains. In this approach, a small molecule covalent label is added to the protein solution and forms covalent bonds with specific amino acid side chains that are exposed to solvent. As compared to HRF, fewer amino acids can react with the covalent label, and typically only one product is generated, which simplifies data analysis and retains sensitivity. Proteolytic cleavage and mass spectrometric analysis can then determine the extent of side chain modification for all peptides and amino acids, allowing for solvent accessibility determinations to be made. Because covalent bonding targets specific side chain functional groups, these studies are often conducted to determine the reactivity of specific residues.

Table 1. A summary of some representative covalent labels and the amino acids that they modify are shown in the table below:

TABLE 1

Examples of Modifying Agents for Amino Acids

| Amino Acid | Reactive Functional Group | Examples of Modifying Agents |
|---|---|---|
| Arginine | guanidinium group | phenylglyoxal, p-hydroxyphenylglyoxal, 2,3-butanedione, 1,2-cyclohexanedione, methylglyoxal |
| Aspartic Acid, Glutamic Acid | carboxylic acid | carbodiimides such as 1-ethyl-3-(3-dimethylaminopropyl)carbodiimide hydrochloride + glycine ethyl ester (GEE) |

TABLE 1-continued

Examples of Modifying Agents for Amino Acids

| Amino Acid | Reactive Functional Group | Examples of Modifying Agents |
|---|---|---|
| Cysteine | Thiol | iodoacetamide and its derivatives, iodoacetic acid, N-alkylmaleimides, chloroacetamide, iodoethanol, others |
| Histidine | Imidazole | diethylpyrocarbonate |
| Lysine | Amine | acetic anhydride, maleic anhydride, succinic anlydride, N-hydroxysuccinimide |
| Tryptophan | Indole | N-bromosuccinimide, o-nitrophenlysulfenyl chloride, Koshland's reagent |
| Tyrosine | Phenol | tetranitromethane, iodine, N-acetylimidazole |

One benefit of this approach is the non-reversibility of the covalent bond that forms. This allows greater flexibility of times, temperatures and pH range to be used at all stages of the sample preparation and analysis when compared to H/D exchange. This also allows for the use of proteolytic enzymes that have greater specificity than pepsin, such as trypsin or chymotrypsin, which serves to simplify data analysis. Another benefit is the relatively large size of the labels themselves. In contrast to deuterium, incorporation of covalent labels onto peptides results in labeled proteins that are easier to detect by mass spectrometry, thereby simplifying data analysis.

Another benefit of this approach is the ease of generating the covalent bond between the covalent label and amino acid side chain functional group. Whereas HRF requires the use of specialized apparatus to generate the hydroxyl radical, covalent bond formation with covalent labels can be accomplished by simply adding the covalent labels to the protein solution.

A further benefit is the relative simplicity of data analysis. Although HRF labeling targets more amino acids, many more different types of products are generated, greatly complicating the mass spectral analysis. In contrast, amino acid specific covalent labeling only adds one label to any given residue, which simplifies identification of labeling sites.

One disadvantage of amino acid specific covalent labeling is that the labels are specific for certain amino acid side chain functional groups. Of the 20 amino acids, only about 14 have side chains that include readily modifiable functional groups. Further, the 14 modifiable side chains are not reactive to the same categories of modifying agents, meaning that most labels will potentially react with only about 3-12% of the amino acids in a protein. Thus, to date, amino acid specific covalent labeling can generally not provide information for all of the amino acids present in a protein in a single assay. This method is especially well suited to examine the activities and/or positions of specific amino acid residues in a given protein, but has been found to be too limited for use as a method for determining the overall HOS of a protein.

Although not as commonly used as the single labeling approach, one technique that has been used to overcome the limitations imposed by the specificity of the single covalent labeling approach is to use more than one label in the protein analysis. This technique involves performing separate experiments, each experiment employing a different modifying agent in isolation with the protein (for example, using EDC and GEE to target glutamic and aspartic acids, and then, in a separate experiment with a fresh supply of unlabeled protein, using maleic anhydride to target lysine. The results from both the glutamic/aspartic acid and lysine labeling experiments can be combined to show the overall impact on both sets of amino acids.)

The use of multiple modifying agents has been previously employed to study protein binding sites, and to determine the relative rates of reaction of various residues toward chemical modification. In general, the purpose of such studies was to further understand the interactions of the residues in protein interactions, or to confirm specific structural aspects of the protein via surface mapping.

Diethylpyrocarbonate (DEPC) has been used for amino acid specific covalent labeling, primarily for studying the role of histidine residues in protein binding interactions. Advances in the use of DEPC for protein surface mapping and ligand binding studies have been recently developed, including reports showing that DEPC is effective at labeling up to 6 different amino acid residues (Cys, Lys, Ser, Thr, His, and Tyr). However, these studies have been limited to protein-protein interactions, and have not considered the potential for DEPC as a label suitable for measuring the overall HOS of a protein. (Mendoza, Antwi, Baron-Rodriguez, and Vachet *Biochemistry.* 2010, 49, 1522-1532); (Mendoza, Baron-Rodriguez, Blanco, and Vachet *Biochemistry.* 2011, 50, 6711-6722)

Mass Spectrometric Comparison of Protein Structure

With the rise of the use of biologics drugs, there has been an increased interest in developing analytical methods that can probe the HOS of proteins with high resolution. Mass spectrometry-based methods such as H/D exchange and HFR have been investigated for this purpose. However, while H/D exchange, HRF, cross-linking and amino acid specific covalent labeling have shown effectiveness at protein surface structural analysis, protein-ligand complex analysis, and protein-protein complex analysis, there is still a need for low cost, reliable methods of comparison of the overall HOS of a protein vs. a reference. Limitations remain with existing methods, especially in situations where assurance is required that the HOS of the protein remains unchanged (for example, when considering a manufacturing process change, when evaluating the potential impact of shipping conditions on protein HOS, or when evaluating a biosimilar). Although amino acid specific covalent labeling has been used for conformational studies for specific amino acid residues and can detect conformational changes, the small number of residues that can be labeled has prevented this method from being used as a stand-alone means of generating high resolution protein HOS studies. Indeed, recent studies claim that amino acid specific covalent labeling is not sufficient as a stand-alone method, but should only be used as a complement to high resolution methods such as H/D exchange or HFR. Other reports that survey or discuss existing methods for HOS analyses for protein therapeutics do not mention amino acid specific covalent labeling in discussions that include other methods such as H/D Exchange, HRF, or Cross-Linking (Zhang, Shen, Rempel, Monsey, Vidaysky, Gross, and Bose *Molecular and Cellular Proteomics,* 2011, 10, M110.005678-1 to 16); (Gau, Garai, Frieden, and Gross *Biochemistry,* 2011, 50, 8117-8126); (Kaur, Kiselar, Shi, Deperalta, Wecksler, Gokulrangan, Ling, and Chance *mAbs,* 2014, 606, 1486-1499); (Shang, Cui, and Gross *FEBS Letters,* 2014, 588, 308-317); (Konermann, Vahidi, and Sowole *Analytical Chemistry,* 2014, 86, 213-232); (Berkowitz, Engen, Mazzeo, and Jones *Nature Reviews: Drug Discovery,* 2012, 11, 527-540)

Mendoza, et al. (2008) relates to an improved diethylpyrocarbonate (DEPC) labeling approach to explore the structural changes directly associated with Cu(II) binding to β-2-microglobulin. See Mendoza and Vachet (2008), Improved Protein Surface Mapping Using Diethylpyrocarbonate with Mass Spectrometric Detection, Anal Chem. 2008 Apr. 15; 80(8): 2895-2904, disclosures of which are incorporated by reference in its entirety to the extent they are not inconsistent with the explicit teachings of this specification.

Mendoza, et al. (2010) relates to a covalent labeling approach to explore the pre-amyloid dimer formation of β-2-microglobulin that are directly associated with Cu(II) binding. See Mendoza, et al., Structure of the Pre-amyloid Dimer of β-2-microglobulin from Covalent Labeling and Mass Spectrometry, Biochemistry, 2010 Feb. 23; 49(7): 1522-1532, disclosures of which are incorporated by reference in its entirety to the extent they are not inconsistent with the explicit teachings of this specification.

Mendoza, et al. (2011) relates to a covalent labeling approach to explore structural insights into the pre-amyloid tetramer of β-2-microglobulin that are directly associated with Cu(II) binding. See Mendoza, et al., Structural Insights into the Pre-amyloid Tetramer of β-2-microglobulin from Covalent Labeling and Mass Spectrometry, Biochemistry, 2011 Aug. 9; 50(31): 6711-6722, disclosures of which are incorporated by reference in its entirety to the extent they are not inconsistent with the explicit teachings of this specification.

Mendoza, et al., demonstrate that the combination of DEPC labeling and MS analysis can be used to determine the impact of ligand binding interactions on the percent labeling of specific amino acid residues. The studies reported by Mendoza, et al., are silent regarding the ability of these techniques to detect global changes in HOS of specific proteins, such as those that may occur during the spontaneous denaturation of therapeutic proteins stored in a condition intended to maintain the structural integrity of these proteins.

The methods disclosed herein can also be used to detect changes and/or differences in the HOS of proteins as may occur during the manufacturing of such proteins (e.g., unformulated therapeutic proteins). These methods can also be used to detect differences been branded protein biologics and functionally similar biosimilar proteins.

This invention enables the use of amino acid specific covalent labeling as a stand-alone method for providing high resolution HOS analyses of proteins. One of the primary shortcomings of amino acid specific covalent labeling in the past was the limited number of residues that could be probed (for example: ~7-8% for lysine-specific labels or ~11% for glutamic/aspartic acid-specific labels). This limitation is especially critical for the biotechnology and pharmaceutical industries, where even small changes in a protein's HOS can have negative impacts on product safety and efficacy. Because DEPC can be used for labeling 6 different amino acid residues, increasing coverage to up to ~30% of amino acids, it enables the use of amino acid specific covalent labeling as a stand-alone method to generate high resolution HOS characterizations of protein structures, including therapeutic proteins and monoclonal antibodies.

In addition, this invention shows that combinations of amino acid specific covalent labels can be used toward the same purpose with expanded coverage of residues, without the need for other methods such as H/D exchange or HRF.

One benefit of this invention is that amino acid specific covalent labeling allows for protein HOS measurements without the need for specialized expertise and/or instrumentation, such as is required for HRF and H/D exchange. Instead, amino acid specific covalent labeling requires only commonly used lab equipment and methodologies, enabling it to be practiced in essentially any lab that routinely conducts mass spectrometric analyses of proteins.

Another benefit of this invention is that protein HOS information can be "locked in" via a simple process of labeling and quenching a small quantity of protein sample. This sample can be frozen and stored/shipped without impacting the results. This is not possible for H/D exchange and would require the presence of a laser or synchrotron source at the point of sampling if HRF was used. This invention therefore enables high resolution protein HOS analyses in locations that do not have direct access to mass spectrometry instrumentation. Instead, samples can be collected and shipped to other locations for mass spectrometric analyses.

Some embodiments of the invention use amino acid specific covalent labeling to map the solvent accessibility of protein amino acids, and then compare the results obtained from this analysis to a reference protein in order to determine the degree of HOS similarity between the targeted proteins. Some embodiments of this method may entail the use of a single small molecule covalent label, or a combination of 2 or more covalent labels. Using multiple covalent labels may serve to increase the % of amino acids that are directly measured using the technique while retaining the benefits of increased robustness and lower costs benefits provided by the conventional covalent bond method.

Some embodiments of the invention will enable practitioners to strategically select one or more small molecule covalent label based on the amino acid composition of the protein. This allows for a targeted effort that is tailored to the specific proteins being studied. This approach is especially useful when the experimentalist is trying to compare the HOS of two or more similar but perhaps not identical 3-dimensional protein structures. Although the use of one or more covalent labels has been previously employed to study protein binding sites, and/or to determine the relative rates of reaction of various residues toward chemical modification, this approach has not been applied to the comparison of the HOS of proteins vs. a reference protein.

Some embodiments of the invention include using the inventive methods to monitor changes including improvements in the manufacturing, storage, or shipping processes that may be desirous, but that may also raise concerns regarding the impact on the HOS of the protein that must be overcome before implementation. In some embodiments these methods can be used to compare protein samples using the current condition of a sample of the protein vs. the proposed conditions in order to determine the impact, or lack of impact, of the proposed conditions on the HOS of the protein. Similarly, this method can be used to help establish the impact of inadvertent changes to the manufacturing, shipping, or storage conditions on the HOS of a protein. In some embodiments these methods can be used to determine if there is any immediate impact (denaturing or aggregation, for instance), and can also be used as a stability indicating method as low levels of denatured or aggregated proteins will be able to be detected. In some embodiments, this method can be used to compare therapeutic protein samples before and after their receipt, handling, and/or formulation in a hospital, pharmacy, or clinic to determine the impact of these activities on the HOS of the protein. Still other embodiments include using the inventive methods to help to determine if a proposed biosimilar compound has the same HOS as the targeted, in this instance branded protein.

Some embodiments of the invention include using the inventive methods to monitor the onset and growth of protein aggregates. In some embodiments these methods can be used to compare protein samples using the current condition of a sample of the protein vs. the proposed conditions in order to identify and monitor residues for which the extent of labeling is correlated to aggregate formation and growth.

In some embodiments of the disclosed subject matter, target proteins may be presented in a suspension buffer that may comprise, without limitation, histidine, citrate and/or phosphate.

In some embodiments, target proteins may be presented in a suspension buffer having a pH of between about 3.5 to about 7.5, or between about 4.5 to 7.5, or between about 5.5 to about 7.5 of between about 5.5 to about 7.3.

Additional buffers may include succinate, acetate, tris, and carbonate.

Amino acids such as histidine, arginine, glycine, methionine, proline, lysine, glutamic acid, alanine, and arginine mixtures may be included in a suspension buffer.

Surfactants such as polysorbates (e.g., Tween-20 or -80), SDS, Brij 35, and Triton X-10 may be included in a suspension buffer.

Stabilizers such as sugars, polyols, metal chelator, and cryoprotectant may also be included in a suspension buffer. Examples of sugars may include, without limitation, glucose, sucrose, trehalose, mannose, and dextrose. Polyols may include, without limitation, sorbitol, mannitol, and glycerol.

Metal chelators may include EDTA. Poloxamers such as Pluronics F-68 and F-127, polyvinylpyrrolidone, alkyl saccharides, and cellulosics may be included in a suspension buffer.

Salts that may be included in a suspension buffer include, without limitation, sodium chloride, calcium chloride, and magnesium chloride.

Polymers and inert proteins such as polyethylene glycols (PEGs), polysaccharides, and inert proteins, may be included in a suspension buffer to non-specifically stabilize proteins and enhance protein assembly. Examples include dextran, hydroxyl ethyl starch (HETA), PEG-4000, and gelatin. Preservatives such as benzyl alcohol, m-cresol, and phenol may be included in a suspension buffer to prevent microbial growth.

In some embodiments of the disclosed subject matter, target proteins may be presented in a lyophilized form.

See Goswami S. et al., Developments and Challenges for mAb-Based Therapeutics, Antibodies 2013, 2:452-500, and see also U.S. Publication No. 2014/0186446, disclosures of both of which are incorporated by reference in its entirety to the extent they are not inconsistent with the explicit teachings of this specification.

The effectiveness of this technology in allowing a comparison of the HOS of proteins can be demonstrated by using proteins with well-defined structures. Examples include low molecular weight proteins such as β-2-microglobulin, mid-range molecular weight proteins such as erythropoietin, and high molecular weight proteins such as IgG1. For each protein, several amino acids will be targeted for covalent labeling, and the results of the HOS structural comparison described in this document will be shown. In addition, forced degradation studies will be conducted for each protein to demonstrate the sensitivity of this method at detecting even a low percentage of conformational difference between proteins being compared.

Example 1: β-2-Microglobulin

β-2-Microglobulin was incubated at 75° C. for 30 min or 1 day for thermal degradation conditions. Heating experiments were also conducted in the presence of a reducing agent, and in this case tris(2-carboxyethyl)phosphine (TCEP) was added after the protein was heated. Oxidative conditions were carried out by incubating the protein in the presence of 3% $H_2O_2$ or 10% $H_2O_2$ (w/w) at room temperature for 1 day. After the forced degradation conditions, the proteins were reacted with DEPC. Stock solutions of DEPC were prepared in acetonitrile. The DEPC reactions of proteins were performed for 1 min at 37° C. and were initiated by adding DEPC in a molar excess of 2.5. The total reaction volume for the experiments was 100 μL, and the total amount of acetonitrile added was 1%. The reactions were quenched after 1 min by adding 10 mM imidazole [14]. The modified proteins were purified using a 10,000 MWCO filter before proteolytic digestion. Since β2m has a disulfide bond, TCEP (protein:TCEP=1:40 molar ratio) was added to reduce the disulfide bond and iodoacetamide was added simultaneously at room temperature for 30 min in the dark to alkylate the reduced Cys residues. The resulting samples were incubated with 10% (vol/vol) acetonitrile at 50° C. for 45 min prior to digestion by immobilized chymotrypsin (enzyme/substrate ratio of 1:10) at 37° C. After 2 h, the reaction mixture was centrifuged for 2 min at 9000 relative centrifugal force to separate the enzyme from the protein. After that, the samples were immediately analyzed by LC-MS. FIGS. 1 through 5 show the results of thermal, oxidative, and reducing degradation studies on the DEPC labeling of beta-2-microglobulin.

Referring now to FIG. 1, % labeling for labeled residues is shown for three conditions, with the native conditions shown in the left-most bar for each residue, heating for 30 minutes in the middle bar, and heating for 1 day in the right-most bar. FIG. 1 shows that thermal degradation conditions (30 min and 1 day thermal) induced changes to the modification percentage of certain amino acids when compared to the native condition. For example, one-day thermal treatment increased the modification percentage of the residue (S20) from about 2% to more than 5% modification in β-2-Microglobulin.

Figure 2:
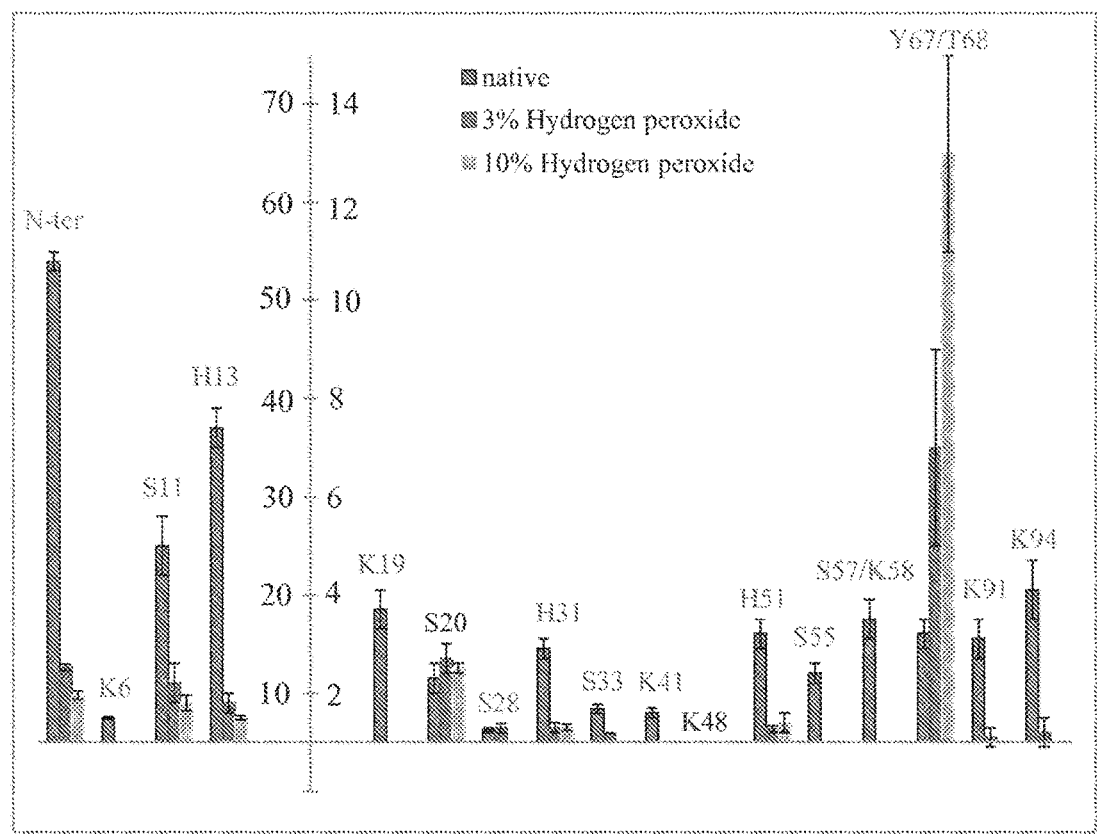
FIG. 2. Bar graph illustrating results from DEPC labeling of β-2-microglobulin that has undergone oxidative degradation.

Referring now to FIG. 2, % labeling for labeled residues is shown for three conditions, with the native conditions shown in the left-most bar for each residue, exposure to 3% hydrogen peroxide in the middle bar, and exposure to 10% hydrogen peroxide in the right-most bar. FIG. 2 shows that oxidative degradation conditions (3% and 10% hydrogen peroxide) induced changes to the modification percentage of certain amino acids when compared to the native conditions. For example, 10% hydrogen peroxide treatment increased the modification percentage of the residues (Y67/T68) from about 3% to more than 12% modification in β-2-Microglobulin.

Example 2: Erythropoietin (EPO)

Figure 3:
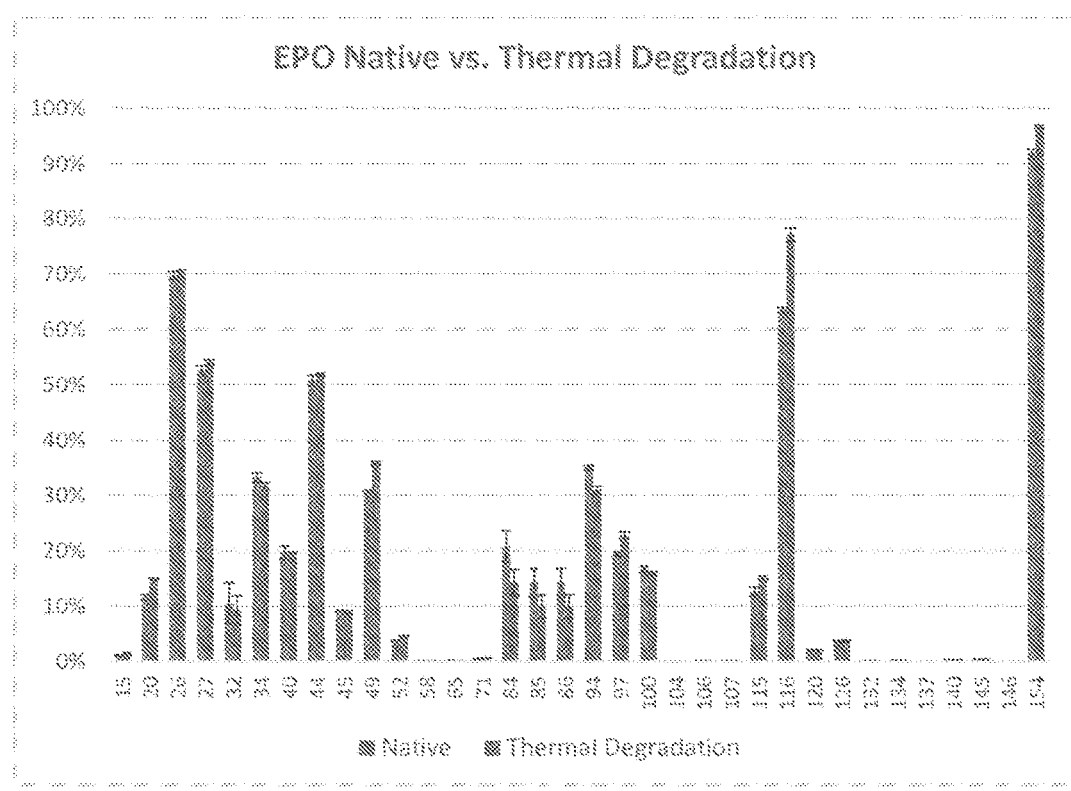
FIG. 3. Bar graph illustrating results from DEPC labeling of Erythropoietin (EPO) that has undergone thermal degradation.

EPO was subject to thermal degradation at 50° C. for 2 hours, with samples processed in the same way as described for β-2-Microglobulin. Referring now to FIG. 3, % labeling for labeled residues is shown for two conditions, with the native conditions shown in the left-most bar for each residue, and thermal degradation conditions in the right-most bar. FIG. 3 shows that thermal degradation condition induced changes to the modification percentage of certain amino acids when compared to the native condition. For example, thermal degradation treatment increased the modification percentage of the residue (116) from about 62% to about 75% modification in EPO.

Example 3: IgG1

Heat Denaturation: IgG1 was analyzed either natively or after being incubated at 75° C. for 15 min.

DEPC Labeling: Labeling for IgG1 was performed using a 0.75 mM solution of DEPC in acetonitrile. The protein solutions had 5 µM IgG1 in 50 mM Phosphate buffer (pH 7.4). These solutions were reacted with DEPC at a 1:4 (protein:DEPC) ratio for 5 min (IgG1) at 22° C. The DEPC reaction was quenched by the addition of imidazole at a 1:50 (DEPC:Imidazole) ratio.

Figure 4:
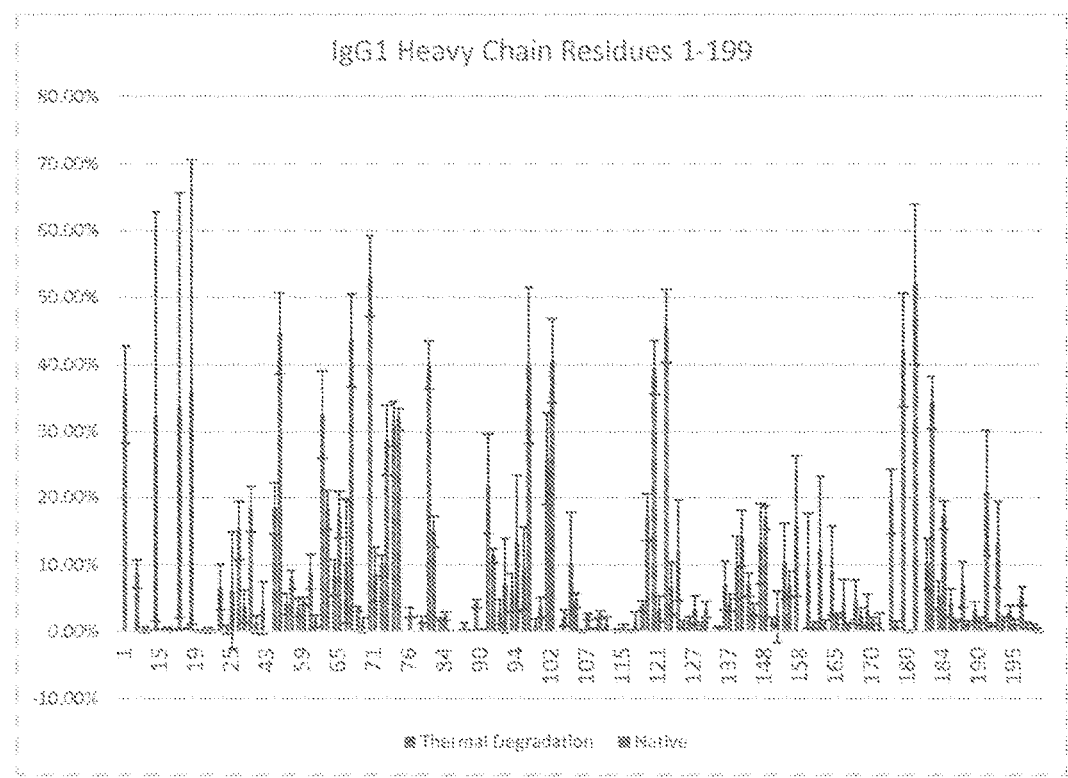
FIG. 4. Bar graph illustrating results from DEPC labeling of IgG1 that has undergone thermal degradation—show labeling results for heavy chain residues 1-199.
Figure 5:
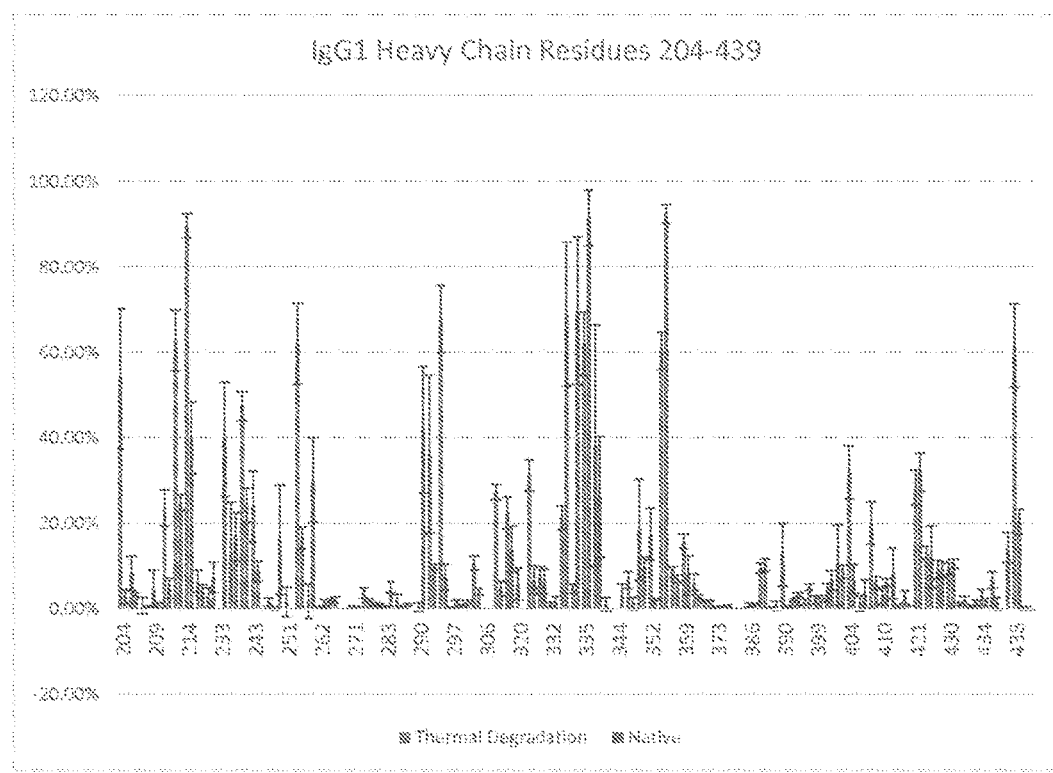
FIG. 5. Bar graph illustrating results from DEPC labeling of IgG1 that has undergone thermal degradation—show labeling results for heavy chain residues 200-435.
Figure 6:
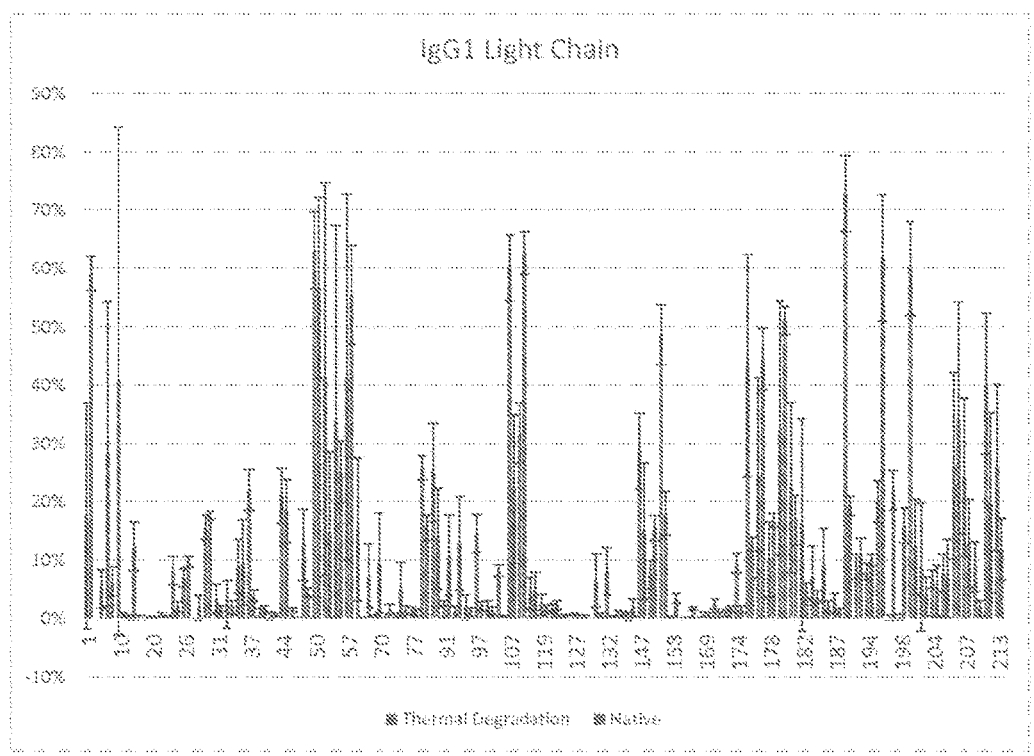
FIG. 6. Bar graph illustrating results from DEPC labeling of IgG1 that has undergone thermal degradation—show labeling results for light chain residues.

Proteolytic Digestion: The digestion was then performed using a 1:100 (papain:protein) ratio for 2.5 hours. Once complete, IgG1 was incubated in a buffered solution (50 mM phosphate buffer at pH 7.4) with 1 M urea, 20 mM DTT, and at 60° C. for 20 min. Next IgG1 was reacted for 2 min with 40 mM iodoacetamide to alkylate the resulting free thiols. Immobilized trypsin was then added to achieve a 1:3 (enzyme:substrate) ratio. The digestion reaction was allowed to proceed overnight at 22° C. After completion the samples were spun at 10000 RPM for 5 min. The supernatant was collected and flash frozen in liquid nitrogen. Each sample was stored at −80° C. until being thawed and immediately analyzed via LCMS Referring now to FIG. 4, FIG. 5, and FIG. 6, % labeling for labeled residues is shown for two conditions, with the thermal degradation conditions shown in the left-most bar for each residue, and native conditions in the right-most bar. FIG. 4 shows that thermal degradation condition induced changes to the modification percentage of heavy chain residues 1-199 when compared to the native condition. Referring now to FIG. 5, thermal degradation condition induced changes to the modification percentage of heavy chain residues 200-435 when compared to the native condition. Referring now to FIG. 6, thermal degradation condition induced changes to the modification percentage of the light chain residues when compared to the native condition.

Figure 7:
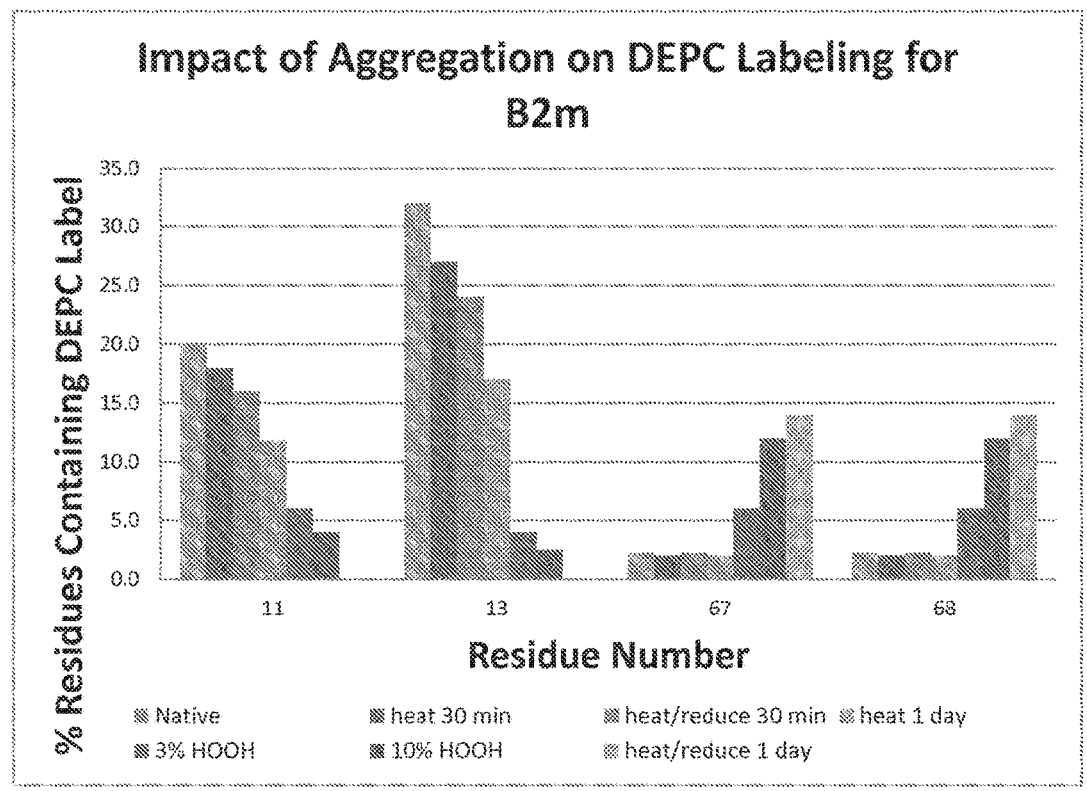
FIG. 7. Bar graph showing modification percentage of specific β-2-Microglobulin amino acids under different degradation conditions.
Figure 8:
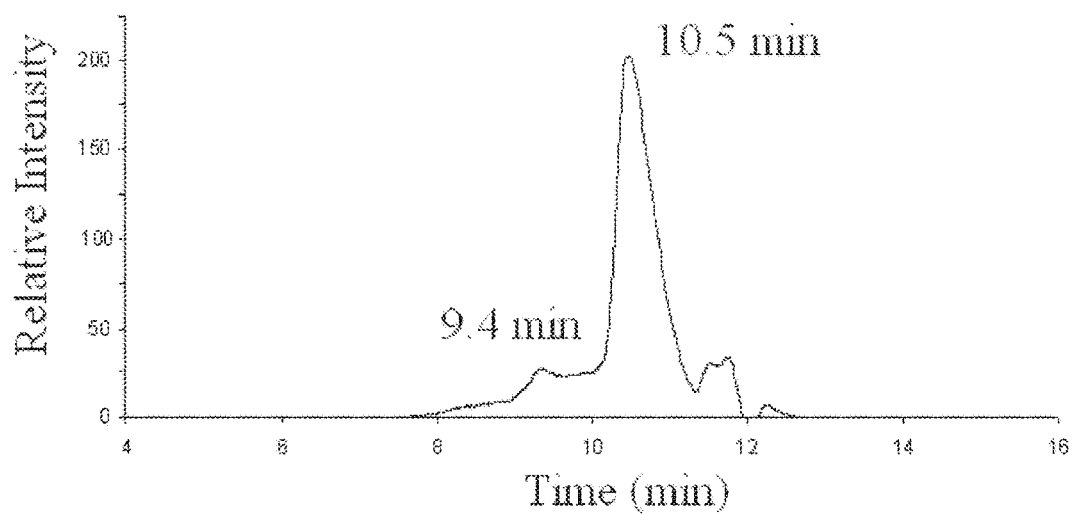
FIG. 8. Graph illustrating results of size exclusion chromatography of β-2-Microglobulin after 1 day at 75° C.
Figure 9:
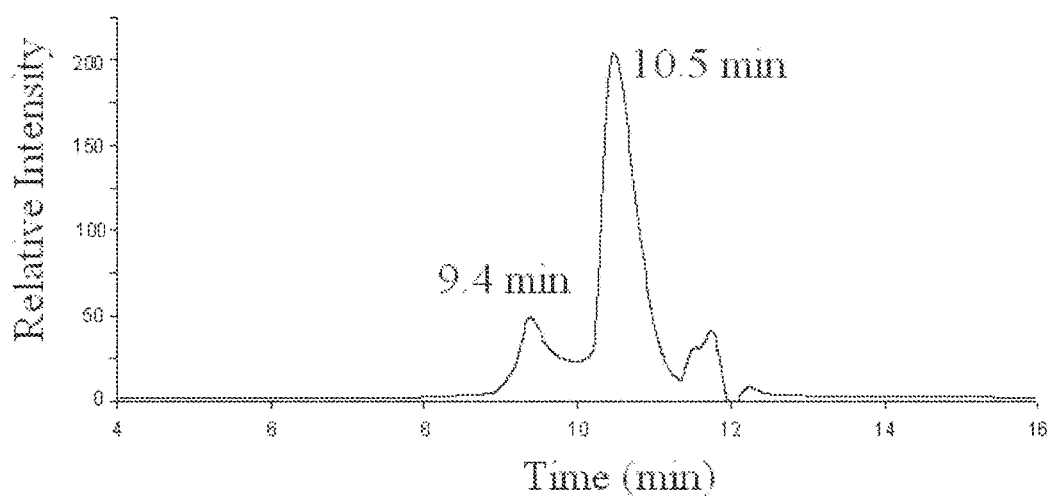
FIG. 9. Graph illustrating results of size exclusion chromatography of β-2-Microglobulin after exposure to 10% hydrogen peroxide.

Example 4: β-2-Microglobulin Aggregation

β-2-Microglobulin samples from the previous example were analyzed for DEPC labeling patterns that correlate with protein aggregation. Additional β-2-Microglobulin degradation samples were generated by repeating the thermal degradation study previously described, but adding a reducing agent (TCEP) prior to labeling to further degrade the protein structure. All subsequent steps were identical to the method described previously for β-2-Microglobulin. Referring now to FIG. 7, % labeling is shown for residues 11, 13, 67, and 68 in the order of increasingly harsh conditions, in which the native conditions are shown via the left-most bar, heating for 30 min via the second bar from the left, heating/reducing 30 min via the third bar from the left, heating for 1 day via the fourth bar from the left, exposure to 3% HOOH via the fifth bar from the left, exposure to 10% HOOH via the sixth bar from the left, and heating/reducing for 1 day via the seventh bar from the left. Still referring to FIG. 7, examination of residues 11 and 13 show a decrease in % labeling as increasingly harsh conditions are employed, while residues 67 and 68 show an increase in % labeling with increasingly harsh conditions. Referring now to FIG. 8, size exclusion chromatography (SEC) data can be used to measure aggregate levels, with peaks eluting before 10 minutes corresponding to β-2-Microglobulin aggregates, while the peak at 10.5 minutes corresponds to the β-2-Microglobulin monomer. Examination of SEC data demonstrates the presence of aggregates in the sample collected after 1 day at 75° C., and an increase in aggregates for the sample collected after exposure to 10% hydrogen peroxide (FIG. 9). Monitoring of % labeling of any of these residues could be used as an indicator of the onset and growth of protein aggregates.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A method for detecting changes in the higher order structure of proteins, comprising the steps of:
    treating a reference protein with diethylpyrocarbonate, under a defined set of conditions, wherein the treating step produces a covalently labeled reference protein;
    contacting a target protein with diethylpyrocarbonate, under the same defined set of conditions that were used with the reference protein, wherein the contacting step produces a covalently labeled target protein, wherein the reference protein and the target protein have identical primary structures, and wherein the proteins are covalently labeled only with diethylpyrocarbonate; and
    analyzing the covalently labeled target protein and the covalently labeled reference protein by mass spectrometry in order to assess the higher order structure of the reference protein and the higher order structure of said target protein.

2. The method according to claim 1, further including the steps of:
    comparing the results of the analysis of the covalently labeled reference protein and the covalently labeled target protein; and
    determining if there is a difference between the higher order structure of the reference protein and the higher order structure of the target protein.

3. The method according to claim 1, wherein the reference protein and the target protein includes at least one amino acid selected from the groups consisting of: cysteine, histidine, lysine, tyrosine, serine, and threonine.

4. The method according to claim 1, wherein the target protein is selected from the group of proteins consisting of: antibodies, enzymes, ligands, and regulatory factors.

5. The method according to claim 1, wherein the reference protein has not been exposed to the same processing or the same manufacturing steps as the target protein.

6. The method according to claim 1, wherein the target protein has been stored in a suspension buffer designed to stabilize the reference protein, or in a lyophilized form for a period of time longer than the time that the reference protein has been stored in the suspension buffer or in a lyophilized form.

7. The method according to claim 6, wherein the suspension buffer include at least one claims of reagent selected from the group of reagents comprising: phosphate, amino acids, inorganic salts, surfactants, metal chelators, polymers, inert proteins, and preservatives.

8. The method according to claim 7, wherein the suspension buffer has a pH in at least one pH range selected from the group consisting of: between about 3.5 to about 7.5; between about 4.5 to about 6.5; and between about 5.5 to about 7.3.

9. The method according to claim 8, wherein the suspension buffer includes at least one of the following amino acids selected from the group consisting of: histidine, arginine, glycine, methionine, proline, lysine, glutamic acid, alanine, and arginine mixtures.

10. The method according to claim 6, wherein the suspension buffer includes at least one of the following inorganic salts selected from the group consisting of: sodium chloride, calcium chloride, and magnesium chloride.

11. The method according to claim 6, wherein the suspension buffer includes at least one of the following surfactants selected from the group consisting of: polysorbates, SDS, Brij 35, and Triton X-10.

12. The method according to claim 6, wherein the suspension buffer includes EDTA as a metal chelator.

13. The method according to claim 6, wherein the suspension buffer includes at least one of the following polymers selected from the group consisting of: polyethylene glycols (PEGs) and polysaccharides.

14. The method according to claim 6, wherein the suspension buffer includes at least one of the following inert proteins selected from the group consisting of: dextran, hydroxyl ethyl starch (HETA), PEG-4000, and gelatin.

15. The method according to claim 6, wherein the suspension buffer includes at least one of the following preservatives selected from the group consisting of: benzyl alcohol, m-cresol, and phenol.

16. The method according to claim 1, further including the step of:
    determining the fraction of the amino acids in the target protein that are labeled as a function of the concentration of the protein and/or the concentration of covalent label modifier in the contacting step.

17. The method according to claim 16, wherein the fraction of the amino acids in the target protein modified by the compound is determined as a function of the time that the target protein and the compound are in contact with one another.

18. The method according to claim 1, wherein one or more of the proteins in the assay has undergone partial degradation or denaturing.

19. The method according to claim 1, wherein an onset and growth of protein aggregates is monitored by percent labeling at one or more amino acids where percent labeling correlates with aggregation.

* * * * *